United States Patent
Kumbhari et al.

(10) Patent No.: US 11,147,578 B2
(45) Date of Patent: Oct. 19, 2021

(54) ENDOSCOPIC GASTRIC MUCOSAL ABLATION/RESECTION/EXCLUSION (A/R/E) AS A MINIMALLY INVASIVE WEIGHT LOSS APPROACH

(71) Applicant: THE JOHNS HOPKINS UNIVERSITY, Baltimore, MD (US)

(72) Inventors: Vivek Kumbhari, Baltimore, MD (US); Anthony N. Kalloo, Baltimore, MD (US); Mouen A. Khashab, Towson, MD (US); Andreas Oberbach, Leipzig (DE)

(73) Assignee: The Johns Hopkins University, Baltimore, MD (US)

( * ) Notice: Subject to any disclaimer, the term of this patent is extended or adjusted under 35 U.S.C. 154(b) by 136 days.

(21) Appl. No.: 15/533,810

(22) PCT Filed: Dec. 8, 2015

(86) PCT No.: PCT/US2015/064427
§ 371 (c)(1),
(2) Date: Jun. 7, 2017

(87) PCT Pub. No.: WO2016/094367
PCT Pub. Date: Jun. 16, 2016

(65) Prior Publication Data
US 2017/0367723 A1 Dec. 28, 2017

Related U.S. Application Data

(60) Provisional application No. 62/088,859, filed on Dec. 8, 2014.

(51) Int. Cl.
*A61B 18/12* (2006.01)
*A61B 17/32* (2006.01)
(Continued)

(52) U.S. Cl.
CPC .. *A61B 17/320016* (2013.01); *A61B 18/1492* (2013.01); *A61B 2018/00261* (2013.01);
(Continued)

(58) Field of Classification Search
CPC .................... A61B 2018/00494; A61F 5/0003
See application file for complete search history.

(56) References Cited

U.S. PATENT DOCUMENTS 5,324,284 A  *  6/1994  Imran ................ A61B 18/1492
                                                        600/374
6,425,853 B1 *  7/2002  Edwards ........... A61B 18/1477
                                                        600/29
(Continued)

FOREIGN PATENT DOCUMENTS

WO       2006068970 A2      6/2006

OTHER PUBLICATIONS

Johnson Stoklossa, Carlene, and Suneet Atwal. "Nutrition care for patients with weight regain after bariatric surgery." Gastroenterology Research and Practice 2013 (2013), hereinafter Johnson. (Year: 2013).*

(Continued)

*Primary Examiner* — Daniel W Fowler
(74) *Attorney, Agent, or Firm* — Harrity & Harrity, LLP (57) ABSTRACT

The present invention is directed to a method of endoscopically ablating/resecting/excluding (A/R/E) the mucosa of the gastric fundus and body. The method of the present invention is intended to cause cellular death to the X/A-like, ghrelin producing and other hormone cells. This is in contrast to present methods to provide only transient ischemia. The use of the method of the present invention results in a more permanent and robust method of reducing ghrelin and other hormone levels. In addition, a method according to the present invention can be used to induce scarring of the (Continued)

gastric fundus which will reduce gastric accommodation of excess food and result in early satiety.

23 Claims, 3 Drawing Sheets

(51) Int. Cl.
  *A61B 18/14* (2006.01)
  *A61B 18/00* (2006.01)
(52) U.S. Cl.
  CPC .............. *A61B 2018/00494* (2013.01); *A61B 2018/00577* (2013.01); *A61B 2018/00982* (2013.01)

(56) References Cited

U.S. PATENT DOCUMENTS

| | | | |
|---|---|---|---|
| 7,571,729 B2 | 8/2009 | Saadat et al. | |
| 7,727,249 B2* | 6/2010 | Rahmani | A61B 17/12013 606/140 |
| 8,568,488 B2* | 10/2013 | Stack | A61F 2/04 623/23.7 |
| 2004/0087936 A1* | 5/2004 | Stern | A61B 18/1492 606/41 |
| 2004/0215180 A1* | 10/2004 | Starkebaum | A61B 18/1492 606/32 |
| 2007/0260112 A1* | 11/2007 | Rahmani | A61B 17/12013 600/104 |
| 2008/0091190 A1* | 4/2008 | Carlton | A61B 17/12022 606/41 |
| 2008/0275445 A1* | 11/2008 | Kelly | A61B 18/1492 606/45 |
| 2009/0012512 A1* | 1/2009 | Utley | A61B 18/1492 606/21 |
| 2009/0276055 A1 | 11/2009 | Harris et al. | |
| 2010/0049224 A1* | 2/2010 | Vargas | A61F 5/0036 606/153 |
| 2010/0081864 A1 | 4/2010 | Hess et al. | |
| 2012/0035249 A1* | 2/2012 | Kuhn | A61B 18/1815 514/44 R |

OTHER PUBLICATIONS

Oberbach A., et al., "Effect of a 4 Week Physical Training Program on Plasma Concentrations of Inflammatory Markers in Patients With Abnormal Glucose Tolerance," European Journal of Endocrinology, Apr. 2006, vol. 154 (4), pp. 577-585.
Oberbach A., et al., "Molecular Fingerprint of High Fat Diet Induced Urinary Bladder Metabolic Dysfunction in a Rat Model," PLoS One, Jun. 2013, vol. 8 (6), pp. e66636.
Oberbach A., et al., "Palmitate Induced IL-6 and MCP-1 Expression in Human Bladder Smooth Muscle Cells Provides a Link Between Diabetes and Urinary Tract Infections," PLoS One, May 2010, vol. 5 (5), pp. e10882.
Oberbach A., et al., "Weight Loss Surgery Improves the Metabolic Status in an Obese Rat Model but Does Not Affect Bladder Fibrosis Associated With High Fat Diet Feeding," International Journal of Obesity, Aug. 2014, vol. 38 (8), pp. 1061-1067.
Pasricha P.J., "Hunger Games: Is Your Stomach Making You Fat?," Gastroenterology, Mar. 2015, vol. 148 (3), pp. 491-493.
Paxton B.E., et al., "Bariatric Embolization for Suppression of the Hunger Hormone Ghrelin in a Porcine Model," Radiology, Feb. 2013, vol. 266 (2), pp. 471-479.
Perry R.J., et al., "The Role of Hepatic Lipids in Hepatic Insulin Resistance and Type 2 Diabetes," Nature, Jun. 2014, vol. 510 (7503), pp. 84-91.
Pillon N.J., et al., "Palmitate-Induced Inflammatory Pathways in Human Adipose Microvascular Endothelial Cells Promote Monocyte Adhesion and Impair Insulin Transcytosis," American Journal of Physiology. Endocrinology and Metabolism, Jul. 2015, vol. 309 (1), pp. E35-E44.
Rizzello M., et al., "Early Postoperative Insulin-Resistance Changes After Sleeve Gastrectomy," Obesity Surgery, Jan. 2010, vol. 20 (1), pp. 50-55.
Ryan K.K., et al., "FXR is a Molecular Target for the Effects of Vertical Sleeve Gastrectomy," Nature, May 2014, vol. 509 (7499), pp. 183-188.
Ryou M., et al., "Current Status of Endoluminal Bariatric Procedures for Primary and Revision Indications," Gastrointestinal Endoscopy Clinics of North America, Apr. 2011, vol. 21 (2), pp. 315-333.
Schaeffer M., et al., "Rapid Sensing of Circulating Ghrelin by Hypothalamic Appetite-modifying Neurons," Proceedings of the National Academy of Sciences of the United States of America, Jan. 2013, vol. 110 (4), pp. 1512-1517.
Schauer P.R., et al., "Bariatric Surgery Versus Intensive Medical Therapy for Diabetes—3-Year Outcomes," The New England Journal of Medicine, May 2014, vol. 370 (21), pp. 2002-2013.
Shah S., et al., "Prospective Controlled Study of Effect of Laparoscopic Sleeve Gastrectomy on Small Bowel Transit Time and Gastric Emptying Half-time in Morbidly Obese Patients With Type 2 Diabetes Mellitus," Surgery for Obesity and Related Diseases, Mar. 2010, vol. 6 (2), pp. 152-157.
Shulman GI., "Ectopic Fat in Insulin Resistance, Dyslipidemia, and Cardiometabolic Disease," The New England Journal of Medicine, Sep. 2014, vol. 371 (12), pp. 1131-1141.
Stefater M.A., et al., "Sleeve Gastrectomy in Rats Improves Postprandial Lipid Clearance by Reducing Intestinal Triglyceride Secretion," Gastroenterology, Sep. 2011, vol. 141 (3), pp. 939-949.
Stefater M.A., et al., "Sleeve Gastrectomy Induces Loss of Weight and Fat Mass in Obese Rats, but Does Not Affect Leptin Sensitivity," Gastroenterology, Jun. 2010, vol. 138 (7), pp. 2426-2436.
Stevanovic D., et al., "Ghrelin-induced Food Intake and Adiposity Depend on Central mTORC1/S6K1 Signaling," Molecular and Cellular Endocrinology, Dec. 2013, vol. 381 (1-2), pp. 280-290.
Stevens J., et al., "US Adults Recommended for Weight Reduction by 1998 and 2013 Obesity Guidelines, NHANES 2007-2012," Obesity (Silver Spring), Mar. 2015, vol. 23 (3), pp. 527-531.
Straub B.K., et al., "Adipophilin/perilipin-2 as a Lipid Droplet-specific Marker for Metabolically Active Cells and Diseases Associated With Metabolic Dysregulation," Histopathology, Mar. 2013, vol. 62 (4), pp. 617-631.
Targher G., et al., "Risk of Cardiovascular Disease in Patients With Nonalcoholic Fatty Liver Disease," The New England Journal of Medicine, Sep. 2010, vol. 363 (14), pp. 1341-1350.
Umemura A., et al., "Effects of Changes in Adipocyte Hormones and Visceral Adipose Tissue and the Reduction of Obesity-Related Comorbidities After Laparoscopic Sleeve Gastrectomy in Japanese Patients With Severe Obesity," Endocrine Journal, 2014, vol. 61 (4), pp. 381-391.
Villar-Gomez E., et al., "Weight Loss Through Lifestyle Modification Significantly Reduces Features of Nonalcoholic Steatohepatitis," Gastroenterology, Aug. 2015, vol. 149 (2), pp. 367-378.
Wang M.C., et al., "Laparoscopic Roux-en-Y Gastric Bypass Versus Sleeve Gastrectomy for Obese Patients With Type 2 Diabetes: A Meta-analysis of Randomized Controlled Trials," The American Surgeon, Feb. 2015, vol. 81 (2), pp. 166-171.
Wilson-Perez H.E., et al., "Vertical Sleeve Gastrectomy Is Effective in Two Genetic Mouse Models of Glucagon-like Peptide 1 Receptor Deficiency," Diabetes, Jul. 2013, vol. 62 (7), pp. 2380-2385.
Wren A.M., et al., "Ghrelin Causes Hyperphagia and Obesity in Rats," Diabetes, Nov. 2001, vol. 50 (11), pp. 2540-2547.
Wren A.M., et al., "Ghrelin Enhances Appetite and Increases Food Intake in Humans," The Journal of Clinical Endocrinology and Metabolism, Dec. 2001, vol. 86 (12), pp. 5992.
Yang J., et al., "Identification of the Acyltransferase That Octanoylates Ghrelin, an Appetite-Stimulating Peptide Hormone," Cell, Feb. 2008, vol. 132 (3), pp. 387-396.
Zechner J.F., et al., "Weight-Independent Effects of roux-en-Y Gastric Bypass on Glucose Homeostasis via Melanocortin-4 Receptors in Mice and Humans," Gastroenterology, Mar. 2013, vol. 144 (3), pp. 580-590.

(56) References Cited

OTHER PUBLICATIONS

Abu D.B.K., et al., "Obesity and Bariatrics for the Endoscopist: New Techniques," Therapeutic Advances in Gastroenterology, Nov. 2011, vol. 4 (6), pp. 433-442.
Acosta S., et al., "Recent Advances in Clinical Practice Challenges and Opportunities in the Management of Obesity," Gut, Apr. 2014, vol. 63 (4), pp. 687-695.
Andrews Z.B., et al., "UCP2 Mediates Ghrelin's Action on NPY/AgRP Neurons by Lowering Free Radicals," Nature, Aug. 2008, vol. 454 (7206), pp. 846-851.
Arble D.M., et al., "Mechanisms Underlying Weight Loss and Metabolic Improvements in Rodent Models of Bariatric Surgery," Diabetologia, Feb. 2015, vol. 58 (2), pp. 211-220.
Arepally A., et al., "Catheter-Directed Gastric Artery Chemical Embolization for Modulation of Systemic Ghrelin Levels in a Porcine Model: Initial Experience," Radiology, Jul. 2007, vol. 244 (1), pp. 138-143.
Arepally A., et al., "Catheter-Directed Gastric Artery Chemical Embolization Suppresses Systemic Ghrelin Levels in Porcine Model," Radiology, Oct. 2008, vol. 249 (1), pp. 127-133.
Ariyasu H., et al., "Stomach is a Major Source of Circulating Ghrelin, and Feeding State Determines Plasma Ghrelin-Like Immunoreactivity Levels in Humans," The Journal of Clinical Endocrinology and Metabolism, Oct. 2001, vol. 86 (10), pp. 4753-4758.
Bado A., et al., "The Stomach Is a Source of Leptin," Nature, Aug. 1998, vol. 394 (6695), pp. 790-793.
Basso N., et al., "First-Phase Insulin Secretion, Insulin Sensitivity, Ghrelin, GLP-1, and PYY changes 72 h After Sleeve Gastrectomy in Obese Diabetic Patients: The Gastric Hypothesis," Surgical Endoscopy, Nov. 2011, vol. 25 (11), pp. 3540-3550.
Bawudun D., et al., "Ghrelin Suppression and Fat Loss After Left Gastric Artery Embolization in Canine Model," Cardiovascular and Interventional Radiology, Dec. 2012, vol. 35 (6), pp. 1460-1466.
Birkenfeld A.L., et al., "Nonalcoholic Fatty Liver Disease, Hepatic Insulin Resistance, and Type 2 Diabetes," Hepatology, Feb. 2014, vol. 59 (2), pp. 713-723.
Cacho J., et al., "Validation of Simple Indexes to Assess Insulin Sensitivity During Pregnancy in Wistar and Sprague-Dawley Rats," American Journal of Physiology. Endocrinology and Metabolism, Nov. 2008, vol. 295 (5), pp. E1269-E1276.
Camilleri M., "Peripheral Mechanisms in Appetite Regulation," Gastroenterology, May 2015, vol. 148 (6), pp. 1219-1233.
Chambers A.P., et al., "Effect of Vertical Sleeve Gastrectomy on Food Selection and Satiation in Rats," American Journal of Physiology. Endocrinology and Metabolism, Oct. 2012, vol. 303 (8), pp. E1076-E1084.
Chambers A.P., et al., "The Effects of Vertical Sleeve Gastrectomy in Rodents Are Ghrelin Independent," Gastroenterology, Jan. 2013, vol. 144 (1), pp. 50-52.
Chambers A.P., et al., "Weight-Independent Changes in Blood Glucose Homeostasis After Gastric Bypass or Vertical Sleeve Gastrectomy in Rats," Gastroenterology, Sep. 2011, vol. 141 (3), pp. 950-958.
Chang B.H., et al., "Protection Against Fatty Liver but Normal Adipogenesis in Mice Lacking Adipose Differentiation-related Protein," Molecular and Cellular Biology, Feb. 2006, vol. 26 (3), pp. 1063-1076.
Colquitt J.L., et al., "Surgery for Weight Loss in Adults," The Cochrane Database of Systematic Reviews, Aug. 2014, vol. 8, pp. CD003641.
Cummings D.E., et al., "A Preprandial Rise in Plasma Ghrelin Levels Suggests a Role in Meal Initiation in Humans," Diabetes, Aug. 2001, vol. 50 (8), pp. 1714-1719.
Cummings D.E., et al., "Plasma Ghrelin Levels After Diet-Induced Weight Loss or Gastric Bypass Surgery," The New England Journal of Medicine, May 2002, vol. 346 (21), pp. 1623-1630.
Cusi K., "Role of Obesity and Lipotoxicity in the Development of Nonalcoholic Steatohepatitis: Pathophysiology and Clinical Implications," Gastroenterology, Apr. 2012, vol. 142 (4), pp. 711-725.
Date Y., et al., "Ghrelin, A Novel Growth Hormone-Releasing Acylated Peptide, is Synthesized in a Distinct Endocrine Cell Type in the Gastrointestinal Tracts of Rats and Humans," Endocrinology, Nov. 2000, vol. 141 (11), pp. 4255-4261.
Date Y., et al., "The Role of the Gastric Afferent Vagal Nerve in Ghrelin-induced Feeding and Growth Hormone Secretion in Rats," Gastroenterology, Oct. 2002, vol. 123 (4), pp. 1120-1128.
De Barros F., et al., "Early Endocrine and Metabolic Changes After Bariatric Surgery in Grade III Morbidly Obese Patients: A Randomized Clinical Trial Comparing Sleeve Gastrectomy and Gastric Bypass," Metabolic Syndrome and Related Disorders, Aug. 2015, vol. 13 (6), pp. 264-271.
De Hollanda A., et al., "Gastrointestinal Hormones and Weight Loss Response After Roux-en-Y Gastric Bypass," Surgery for Obesity and Related Diseases, Sep.-Oct. 2014, vol. 10 (5), pp. 814-819.
Dornonville C., et al., "Ghrelin Treatment Reverses the Reduction in Weight Gain and Body Fat in Gastrectomised Mice," Gut, Jul. 2005, vol. 54 (7), pp. 907-913.
Elliott R.M., et al., "Glucagon-like Peptide-1 (7-36)amide and Glucose-dependent Insulinotropic Polypeptide Secretion in Response to Nutrient Ingestion in Man: Acute Post-prandial and 24-h Secretion Patterns," Journal of Endocrinology, Jul. 1993, vol. 138 (1), pp. 159-166.
Faleck D.M., et al., "Adipose Differentiation-related Protein Regulates Lipids and Insulin in Pancreatic Islets," American Journal of Physiology-Endocrinology and Metabolism, Aug. 2010, vol. 299 (2), pp. E249-E257.
Fasshauer M., et al., "Adipokines in Health and Disease," Trends in Pharmacological Sciences, Jul. 2015, vol. 36 (7), pp. 461-470.
Flegal K.M., et al., "Prevalence of Obesity and Trends in the Distribution of Body Mass Index Among US Adults, 1999-2010," JAMA, Feb. 2012, vol. 307 (5), pp. 491-497.
Gao D., et al., "The Effects of Palmitate on Hepatic Insulin Resistance Are Mediated by NADPH Oxidase 3-derived Reactive Oxygen Species Through JNK and p38MAPK Pathways," Journal of Biological Chemistry, Sep. 2010, vol. 285 (39), pp. 29965-29973.
Gibbs J., et al., "Cholecystokinin Decreases Food Intake in Rats," Journal of Comparative and Physiological Psychology, Sep. 1973, vol. 84 (3), pp. 488-495.
Gonzalez C.R., et al., "Influence of Chronic Undernutrition and Leptin on GOAT mRNA Levels in Rat Stomach Mucosa," Journal of Molecular Endocrinology, Dec. 2008, vol. 41 (6), pp. 415-421.
Grayson B.E., et al., "Weight Loss by Calorie Restriction Versus Bariatric Surgery Differentially Regulates the Hypothalamo-pituitary-adrenocortical Axis in Male Rats," Stress, Dec. 2014, vol. 17 (6), pp. 484-493.
Hosoda H. et al., "Ghrelin and Des-acyl Ghrelin: Two Major Forms of Rat Ghrelin Peptide in Gastrointestinal Tissue," Biochemical and Biophysical Research Communications, Dec. 2000, vol. 279 (3), pp. 909-913.
Johnston B.C., et al., "Comparison of Weight Loss Among Named Diet Programs in Overweight and Obese Adults: A Meta-Analysis," JAMA, Sep. 2014, vol. 312 (9), pp. 923-933.
Kitazawa T., et al., "Correlation of Ghrelin Concentration and Ghrelin, ghrelin-O-acetyltransferase (GOAT and Growth Hormone Secretagogue Receptor 1A mRNAs Expression in the Proventriculus and Brain of the Growing Chicken," Peptides, Jan. 2015, vol. 63, pp. 134-142.
Kojima M., et al., "Ghrelin is a Growth-Hormone-Releasing Acylated Peptide From Stomach," Nature, Dec. 1999, vol. 402 (6762), pp. 656-660.
Korner J., et al., "Effects of Roux-en-Y Gastric Bypass Surgery on Fasting and Postprandial Concentrations of Plasma Ghrelin, Peptide YY, and Insulin," The Journal of Clinical Endocrinology and Metabolism, Jan. 2005, vol. 90 (1), pp. 359-365.
Kuppens R.J., et al., "Elevated Ratio of Acylated to Unacylated Ghrelin in Children and Young Adults With Prader-willi Syndrome," Endocrine, Dec. 2015, vol. 50 (3), pp. 633-642.
Lassailly G., et al., "Bariatric Surgery Reduces Features of Nonalcoholic Steatohepatitis in Morbidly Obese Patients," Gastroenterology, Aug. 2015, vol. 149 (2), pp. 379-388.

(56) References Cited

OTHER PUBLICATIONS

Lee T.F., et al., "Downregulation of Hepatic Stellate Cell Activation by Retinol and Palmitate Mediated by Adipose Differentiation-related Protein (ADRP)," Journal of Cellular Physiology, Jun. 2010, vol. 223 (3), pp. 648-657.

Lito K.M., "Weight Loss Surgery: Is This the Eve of the Sleeve?," Today's Dietician, Sep. 2008, vol. 10 (9), pp. 56.

Meydan C., et al., "Immediate Metabolic Response Following Sleeve Gastrectomy in Obese Diabetics," Obesity Surgery, Nov. 2015, vol. 25 (11), pp. 2023-2029.

Mozaffarian D., et al., "Changes in Diet and Lifestyle and Long-term Weight Gain in Women and Men," The New England Journal of Medicine, Jun. 2011, vol. 364 (25), pp. 2392-2404.

Muller T.D., et al., "Ghrelin," Molecular Metabolism, Mar. 2015, vol. 4 (6), pp. 437-460.

Myronovych A., et al., "Vertical Sleeve Gastrectomy Reduces Hepatic Steatosis While Increasing Serum Bile Acids in a Weight-Loss-Independent Manner," Obesity (Silver Spring), Feb. 2014, vol. 22 (2), pp. 390-400.

Nakazato M., et al., "A Role for Ghrelin in the Central Regulation of Feeding," Nature, Jan. 2001, vol. 409 (6817), pp. 194-198.

Neary N.M., et al., "Ghrelin Increases Energy Intake in Cancer Patients With Impaired Appetite: Acute, Randomized, Placebo-controlled Trial," The Journal of Clinical Endocrinology and Metabolism, Jun. 2004, vol. 89 (6), pp. 2832-2836.

Ng M., et al., "Global, Regional, and National Prevalence of Overweight and Obesity in Children and Adults During 1980-2013: A Systematic Analysis for the Global Burden of Disease Study 2013," Lancet, Aug. 2014, vol. 384 (9945), pp. 766-781.

\* cited by examiner

ENDOSCOPIC GASTRIC MUCOSAL ABLATION/RESECTION/EXCLUSION (A/R/E) AS A MINIMALLY INVASIVE WEIGHT LOSS APPROACH

CROSS-REFERENCE TO RELATED APPLICATIONS

This application is a 35 U.S.C. § 371 U.S. national entry of International Application PCT/US2015/064427, having an international filing date of Dec. 8, 2015, which claims the benefit of U.S. Provisional Application No. 62/088,859, filed Dec. 8, 2014, the content of each of the aforementioned applications is herein incorporated by reference in their entirety.

FIELD OF THE INVENTION

The present invention relates generally to medical devices. More particularly, the present invention relates to a device and method for treatment of obesity and its associated comorbidities.

BACKGROUND OF THE INVENTION

There are 40 known hormones that are secreted to inhibit the sensation of hunger. There is only one hormone that is known to promote it—ghrelin. Ghrelin is a peptide produced by ghrelin cells in the mucosa of the gastric fundus and body as well as other areas in the gastrointestinal tract in response to hunger and starvation. Approximately 75% of ghrelin is produced in the gastric fundus and body. Ghrelin increases feelings of hunger, and increases gastric acid secretion and gastrointestinal motility to prepare the body for food intake. Ghrelin is secreted when the stomach is empty. Secretion stops when the stomach is stretched. In addition to ghrelin, there are likely other hormones that are secreted or regulated by the gastric mucosa. It is possible that the benefits seen with a sleeve gastrectomy are due to the removal of the gastric mucosa as opposed to simply a reduction in size of the stomach. Therefore, A/R/E of the gastric mucosa may be a method of regulating hormones for the purposes of treating obesity and its comorbidities.

Investigation in pre-clinical models (swine and canine) are being carried out to determine if angiographic catheter based embolization of the arterial supply to the gastric fundus is effective in decreasing ghrelin, hence reducing appetite and promoting weight loss. The published results are promising thus far. However, this is an invasive method of causing ischemia and decreasing ghrelin production. Additionally, only transient ischemia is being achieved as opposed to more permanent destruction of the X-A like cells (cells that secrete ghrelin).

Accordingly, there is a need in the art for a method and apparatus for destruction of the mucosa of the stomach in order to generate weight loss.

SUMMARY OF THE INVENTION

The foregoing needs are met by the present invention which provides a method for treating obesity and its comorbidities in a subject including inserting an endoscope through the mouth and the esophagus and advancing the endoscope to a region of treatment. The method also includes treating ghrelin and other hormone producing cells of the gastric mucosa disposed in the region of treatment. Additionally, the method includes reducing food intake for the subject and inducing weight loss and improvement in metabolic parameters in the subject.

In accordance with an aspect of the present invention, the method includes reducing ghrelin and other hormone producing cells disposed in the region of treatment by ablating the gastric mucosa. The method can include reducing ghrelin and other hormone producing cells disposed in the region of treatment by treating the area with a topical gel or solution to induce cell death. The method can also include treating ghrelin producing cells disposed in the region of treatment by resecting the mucosa of a gastric fundus of the subject. Additionally, the method can include treating ghrelin producing cells disposed in the region of treatment by creating a submucosal tunnel to separate gastric mucosa from submucosa to allow a resulting space to be filled with a solution or a gel to act as a barrier or result in cell death.

In accordance with another aspect of the present invention, inducing weight loss and hormonal changes includes excluding food and other oral nutrients from coming into contact with the gastric mucosa. The method also includes reducing stomach capacity. The method can also include using an imaging tool to visualize the region of treatment. The gastric fundus and body are targeted as the region of treatment. In addition, the method can include removing ghrelin and other hormone producing cells from the region of treatment.

In accordance with yet another aspect of the present invention, the method includes removing all ghrelin producing cells. A percentage of ghrelin producing cells for removal can be predetermined. The number of ghrelin producing cells in the region of treatment can also be reduced. The method includes monitoring ghrelin and other hormone levels and food intake after the reduction of ghrelin and other hormone producing cells in the region and subsequent reduction of ghrelin producing cells can also be performed. The percentage of ghrelin and other hormone producing cells can be reduced incrementally. The method can include using tools with radiopaque labeling for visualization. The method includes predetermining an amount of gel or solution to cause the desired cell death. Additionally, the method can include labelling the ghrelin and other hormone producing cells for visualization. The method includes using both ablation and a solution or gel that cause death of ghrelin and other hormone producing cells to reduce the number of ghrelin and other hormone producing cells. The method can further include reducing ghrelin and other hormone production or selectively deactivating ghrelin and other hormone producing cells. The method also includes altering gastric compliance.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains, having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to a method of endoscopically ablating/resecting/excluding (A/R/E) the mucosa of the gastric fundus and body. The method of the present invention is intended to cause cellular death to the gastric mucosa. This is in contrast to present methods to provide only transient ischemia. The use of the method of the present invention results in a more permanent and robust method of devitalizing the gastric mucosa. In addition, a method according to the present invention can be used to induce scarring of the gastric mucosa and submucosa which will reduce gastric accommodation of excess food and result in early satiety.

More particularly, the present invention is directed to a method of ablation/resection/exclusion (A/R/E) of the mucosa of the gastric fundus and body, where ghrelin and other hormone producing cells are located. According to a method of the present invention A/R/E is performed endoscopically. An endoscope is inserted through the mouth and then the esophagus and then into the stomach of the patient. A tool for creating A/R/E in the gastric fundus and body is inserted into or attached to or inserted under the guidance of the endoscope. An imaging device can also be employed, in order to visualize the A/R/E procedure and the area being treated. Methods of ablation include thermal techniques such as argon plasma coagulation, cryoablation, and radiofrequency ablation. Any suitable method of A/R/E known to or conceivable to one of skill in the art can also be used. These methods result in tissue death. The amount of tissue death created depends on the dosage of ablation applied.

The present invention can also include application of a topical solution or gel that will result in cellular death in the gastric fundus and body. Again, the amount of cell death created depends on the dosage applied to the region. According to a method of the present invention an endoscope is inserted through the mouth and then the esophagus and then the stomach of the patient. A tool for applying the topical solution or gel in the gastric fundus is inserted into or attached to or inserted under the guidance of the endoscope. An imaging device can also be employed, in order to visualize the application of the solution or gel and the area being treated. Any suitable solution or gel for causing cell death known to or conceivable by one of skill in the art can be used.

The present method is also directed to a method of reducing or eliminating ghrelin and other hormone producing cells in the gastric fundus by resecting the mucosa of the gastric fundus and body endoscopically via endoscopic mucosal resection. According to a method of the present invention an endoscope is inserted through the mouth and then into the esophagus and then into the stomach of the patient. A tool or tools for resecting the mucosa can be inserted to the treatment area through or attached to or inserted under the guidance of the endoscope. An imaging device, such as an x-ray or computed tomography (CT) scanner, can also be employed, in order to visualize the resection of the mucosa and the area being treated. Any suitable tool or tools for resecting the mucosa known to or conceivable by one of skill in the art can be used. The tools used can include radiopaque labelling in order to visualize their movements with the imaging device. The ghrelin producing cells can also be labeled for increased visualization.

The method can also include using an endoscopically created submucosal tunnel to separate the gastric mucosa from the submucosa to allow this space to be filled with a solution or gel which will act as a barrier to devitalize the mucosa of the stomach and result in cell death. According to a method of the present invention an endoscope is inserted through the mouth and then through the esophagus and then the stomach of the patient. A tool or tools for creating a submucosal tunnel are inserted through or attached to or inserted under the guidance of endoscope and to the treatment area. An imaging device can also be employed, in order to visualize the creation of the submucosal tunnel and the area being treated. Any suitable tool or tools known to or conceivable by one of skill in the art can be used.

The present invention can also include a method of excluding food and other oral nutrients from coming into contact with the stomach. According to a method of the present invention an endoscope is inserted through the mouth and then into an esophagus of the patient. A tool or tools for excluding food and other oral nutrients from coming into contact with the stomach are inserted into or attached to or inserted under the guidance of the endoscope and to the treatment area. An imaging device can also be employed, in order to visualize the area being treated. Any suitable tool or tools known to or conceivable by one of skill in the art can be used.

Figure 1:
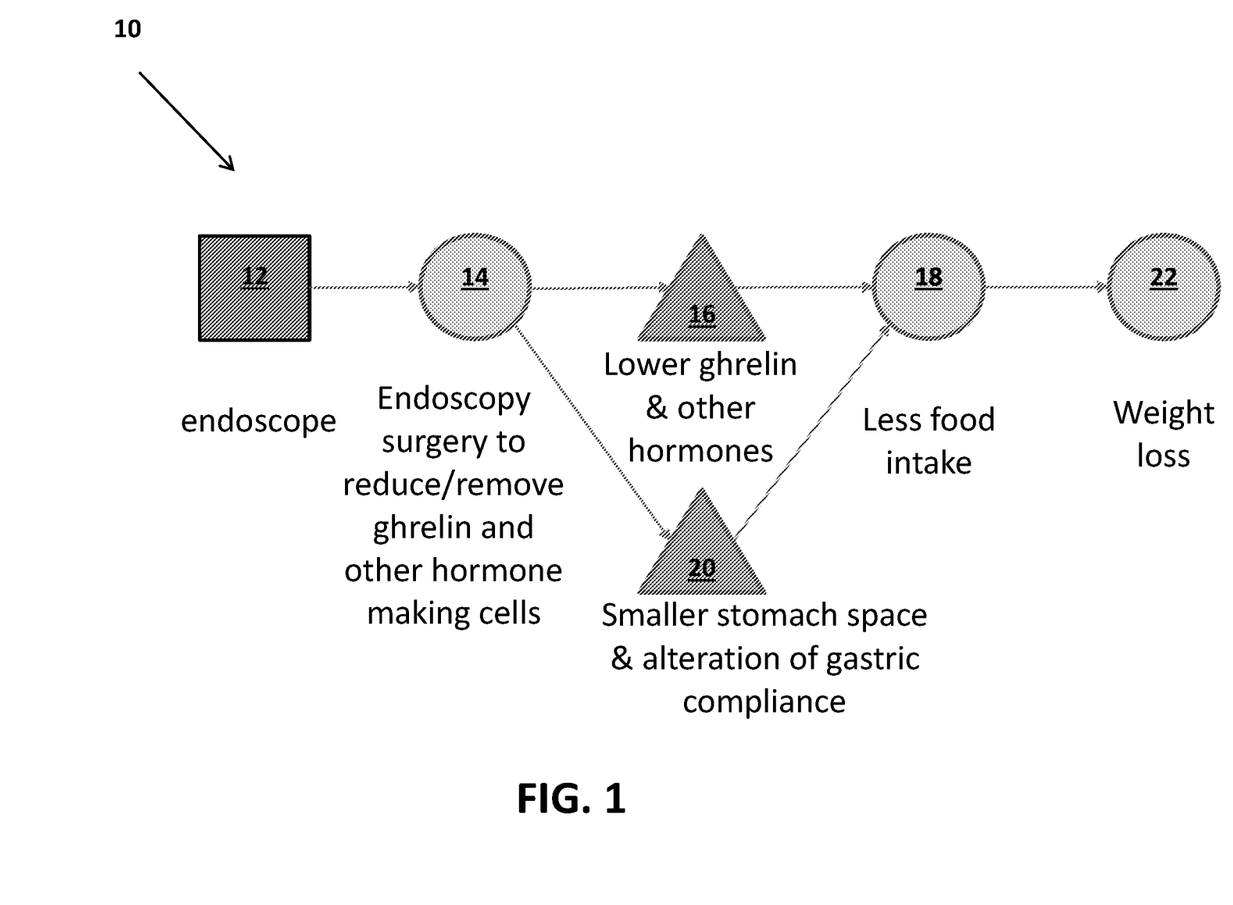
FIG. 1 illustrates a schematic diagram of a method of treating obesity and its associated comorbidities according to an embodiment of the present invention.

FIG. 1 illustrates a schematic diagram of a method for treating obesity, according to an embodiment of the present invention. As illustrated in FIG. 1, the method 10 includes use of an endoscope 12. The endoscope 12 is inserted into through the mouth and then into an esophagus of the subject and advanced to the treatment site. The method 10 also includes endoscopy surgery to reduce/or remove ghrelin and other hormone producing cells 14. The ghrelin producing cells may be reduced, removed, or deactivated according to the methods described above, such as ablation, resection, or exclusion, or in any other suitable manner known to or conceivable by one of skill in the art. The reduction, removal, or deactivation of the ghrelin and other hormone producing cells can be selective, with only some of the cells being targeted. Reduction, removal, or deactivation of the ghrelin and other hormone producing cells can lower ghrelin and other hormone levels 16 and also create a smaller stomach space 20. The reduction of the hormones and also the reduction of stomach space results in reduced food intake and weight loss. Therefore, it should also be noted that the ghrelin and other hormone producing cells need not be removed completely. A determination of the percentage of ghrelin and other hormone producing cells to be removed, reduced, or deactivated can be included as a part of this method. Cell removal/reduction can also be incremental with a percentage of ghrelin and other hormone producing cells being removed, reduced, or deactivated over a number of endoscopic procedures. Decrease in ghrelin and other hormone production and appetite can be monitored between procedures. Decrease in ghrelin and other hormone levels 16 and smaller stomach space 20 results in less food intake 18 and weight loss 22. Weight loss 22 serves to fight obesity and obesity-related diseases such as diabetes.

It should be noted that the procedure of the present invention also decreases compliance of the gastric fundus and body as in step 20. In more detail, by decreasing compliance, one may affect the stomach's response to stretch that occurs during food ingestion. The decreased compliance reduces the ability of the stomach to accommodate contents and thereby this triggers an early or exaggerated stimulus from gastric stretch receptors to the brain, triggering early satiety and a reduction in food intake. It also triggers an exaggerated neurohormonal response. The submucosal fibrosis induced by A/R/E decreases compliance. Aside from fibrosis, injection of material into the submucosa (gel, solution) is also a way of decreasing compliance.

Figure 2:
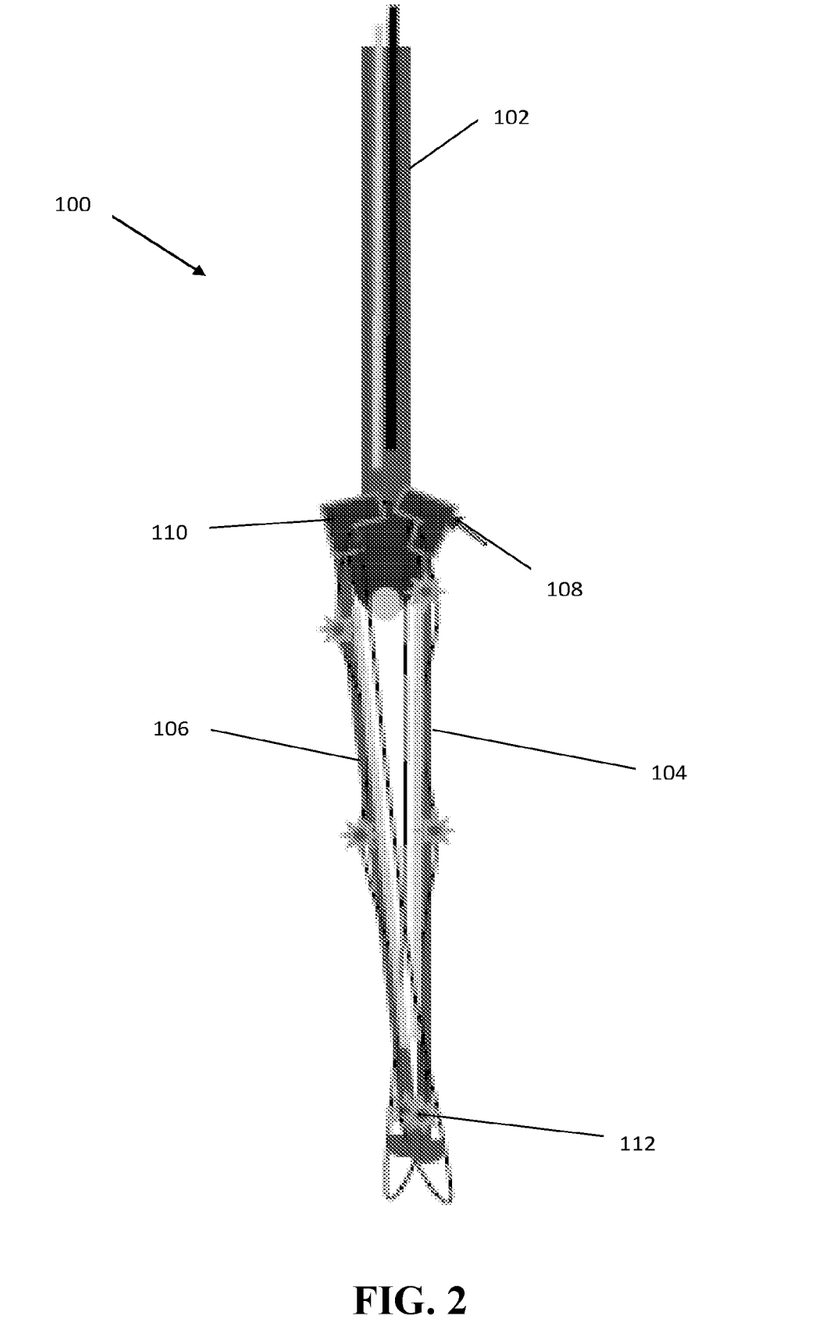
FIG. 2 illustrates a device and scope according to an embodiment of the present invention in a closed position.
Figure 3:
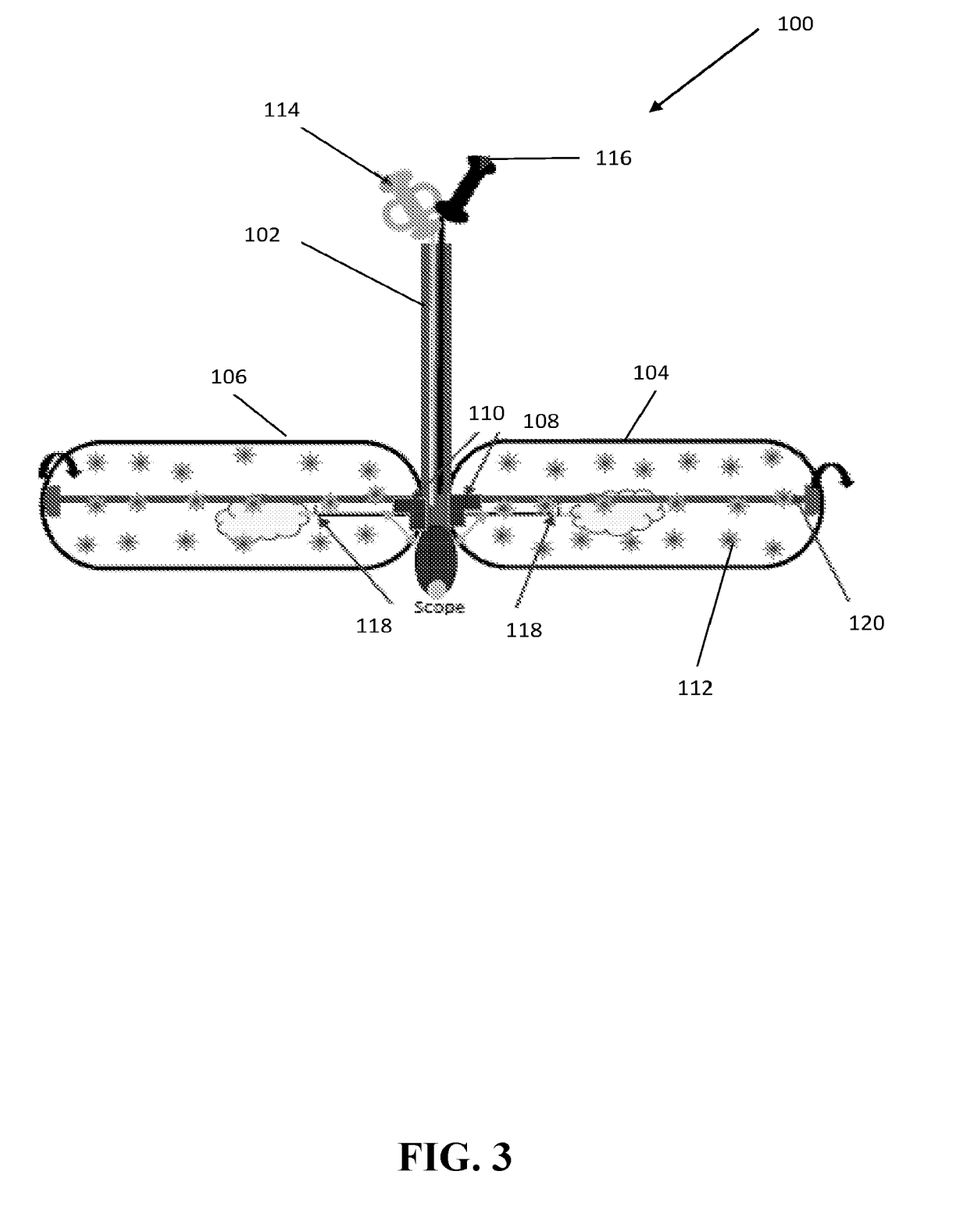
FIG. 3 illustrates a device and scope according to an embodiment of the present invention in a ready position.

FIG. 2 illustrates a device and scope according to an embodiment of the present invention in a closed position and FIG. 3 illustrates a device and scope according to an embodiment of the present invention in a ready position. Generally, the device includes small stiff catheter with two deflated balloons (2 cm wide) on each side of it. On the surface of these balloons are multiple electrodes which conduct thermal energy to the tissue. Once the catheter exists the endoscope tip, the balloons are inflated with air or a fluid solution and expand perpendicular to the endoscope. The balloons are able to roll over tissue. Then, the catheter is connected to current and you simply roll the device over tissue and hence ablate in an efficient and uniform manner.

More particularly with respect to FIGS. 2 and 3, the device 100 includes an elongated catheter 102 with balloons 104 and 106 at the distal end to be advanced to the treatment site. The balloons 104 and 106 are disposed on stiff arms 120 and attached to the catheter with hinges 108 and 110. Electrodes 112 are disposed over the surface of balloons 104 and 106 and deliver treatment to the desired locations. The electrodes 112 can be activated selectively or all activated to provide treatment. Power is delivered to the electrodes 112 via element 116. Inflators 118 deliver air or a fluid solution from element 114 in order to inflate the balloons 104 and 106. One way valves maintain stability for the inflation. As the balloons inflate hinges 108 and 110 are extended and the balloons 104 and 106 extend perpendicular to catheter 102. The device 100 is navigated to the treatment site with the balloons 104 and 106 in a downward position in line with the catheter 102. The hinges 108 and 110 are locked to maintain this position during insertion. Inflation unlocks the arms from the downward position of insertion and extends them to the perpendicular ready position. When the procedure is complete, the balloons 104 and 106 can be deflated and relocked in the downward position for removal. Internal frame 20 allows the device to roll forward and backwards with the scope. Ideally, the device should be able to go "through-the scope" (i.e. using the working channel which can be as large as 3.8 mm). However, the invention should be considered to include the device being attached to the outside of the scope.

The procedure has the following outcomes in rats and pigs. The procedure causes reduction in food intake and reduction in weight or reduced capacity for weight regain after initial weight loss. The procedure results in a reduction in visceral and subcutaneous adiposity. The procedure results in improved serum lipid profile and reduced liver lipid content. The procedure results in improved glucose metabolism and decreased fecal fat absorption.

It should be noted that the present invention is also directed to devices to facilitate mucosal ablation of the gastric fundus and body a more efficient procedure, devices that cover and exclude the gastric fundus from contact with nutrients, devices that cause scarring of damage the gastric fundal and body mucosa, and products that can be injected into the submucosa to cause scarring or damage the mucosa of the gastric fundus and body.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for treating obesity and metabolic disease in a subject, comprising:
   inserting an endoscope through a mouth of the subject and into an esophagus of the subject;
   advancing the endoscope to a region of treatment, wherein the region of treatment includes gastric mucosa associated with a gastric fundus and body;
   forming a barrier by inserting material into gastric submucosa of the gastric fundus and body to:
      separate the gastric mucosa from layers deeper than the gastric submucosa; and
   selectively treating the gastric mucosa by ablating, resecting, or excluding at least a portion of the gastric mucosa in the region of treatment to thereby cause: scarring sufficient to decrease compliance associated with a stomach of the subject, to reduce stretching of the stomach during food ingestion, and to reduce an ability of the stomach to accommodate contents, and reduction of a stomach capacity of the subject,
   wherein the barrier reduces treatment in the layers deeper than the gastric submucosa.

2. The method of claim 1 wherein selectively treating the gastric mucosa comprises treating the region of treatment with a topical gel or solution to induce cell death.

3. The method of claim 1 further comprising using an imaging tool to visualize the region of treatment.

4. The method of claim 3 further comprising labelling for visualizing hormone producing cells.

5. The method of claim 1 further comprising predetermining an amount of gel or solution to cause a predetermined cell death.

6. The method of claim 1 further comprising using both ablation and a solution or gel to treat the gastric mucosa.

7. The method of claim 1, further comprising:
   monitoring a ghrelin level after selectively treating the gastric mucosa; and
   performing subsequent procedures based on the ghrelin level.

8. A method for treating obesity and metabolic disease in a subject, comprising:
   inserting an endoscope through a mouth of the subject and into an esophagus of the subject;
   advancing the endoscope to a region of treatment;
   targeting a gastric fundus and body as the region of treatment;
   forming a barrier by inserting material into gastric submucosa of the gastric fundus and body to separate gastric mucosa of the gastric fundus and body from layers deeper than the gastric submucosa; and selectively treating the gastric mucosa by ablating, resecting, or excluding at least a portion of the gastric mucosa in the region of treatment to thereby cause scarring sufficient to reduce an ability of a stomach of the subject to accommodate contents and to reduce of a stomach capacity of the subject, wherein the barrier reduces treatment in the layers deeper than the gastric submucosa.

9. The method of claim 8, wherein selectively treating the gastric mucosa comprises treating the region of treatment with a topical gel or solution to induce cell death.

10. The method of claim 9, further comprising:

determining a predetermined amount of the topical gel or solution to cause a predetermined amount of cell death; and wherein treating the region of treatment with the topical gel or solution to induce cell death comprises:

treating the region of treatment with the predetermined amount of the topical gel or solution to cause the predetermined amount of cell death.

11. The method of claim 8, further comprising using an imaging tool to visualize the region of treatment.

12. The method of claim 8, further comprising:

labelling for visualizing hormone producing cells.

13. The method of claim 8, wherein the scarring is sufficient to trigger an early and exaggerated stimulus from gastric stretch receptors to a brain of the subject.

14. The method of claim 8, wherein selectively treating the gastric mucosa causes a reduction in the stomach capacity of the subject.

15. The method of claim 8, further comprising:

determining a percentage of ghrelin to be removed; and performing incremental surgeries based on determining the percentage of ghrelin to be removed.

16. A method for treating obesity and metabolic disease in a subject, comprising:

inserting an endoscope through a mouth of the subject and into an esophagus of the subject;

advancing the endoscope to a region of treatment, wherein the region of treatment includes gastric mucosa associated with a gastric fundus and body;

forming a barrier by inserting material into gastric submucosa of the gastric fundus and body to separate the gastric mucosa from layers deeper than the gastric submucosa; and selectively treating the gastric mucosa by ablating, resecting, or excluding at least a portion of the gastric mucosa in the region of treatment to thereby cause scarring sufficient to decrease compliance associated with a stomach of the subject, wherein the barrier reduces treatment in the layers deeper than the gastric submucosa, and wherein selectively treating the gastric mucosa causes a reduction in a stomach capacity of the subject.

17. The method of claim 16, wherein selectively treating the gastric mucosa comprises treating the region of treatment with a topical gel or solution to induce cell death.

18. The method of claim 17, further comprising:

determining a predetermined amount of the topical gel or solution to cause a predetermined amount of cell death; and wherein treating the region of treatment with the topical gel or solution to induce cell death comprises:

treating the region of treatment with the predetermined amount of the topical gel or solution to cause the predetermined amount of cell death.

19. The method of claim 16, further comprising using an imaging tool to visualize the region of treatment.

20. The method of claim 16, further comprising:

labelling for visualizing hormone producing cells.

21. The method of claim 16, wherein selectively treating the gastric mucosa causes a reduction in stretching of the stomach of the subject during food ingestion, and a reduction in an ability of the stomach to accommodate contents.

22. The method of claim 16, wherein ghrelin cells are labeled for increased visualization.

23. The method of claim 16, wherein selectively treating the gastric mucosa by ablating, resecting, or excluding at least the portion of the gastric mucosa comprises:

selectively ablating at least the portion of the gastric mucosa via argon plasma coagulation ablation.

* * * * *